United States Patent
Freed et al.

[11] Patent Number: 5,833,619
[45] Date of Patent: Nov. 10, 1998

[54] EXTERNAL BLOOD PRESSURE SENSOR APPARATUS AND METHOD

[75] Inventors: Paul S. Freed, Bloomfield Hills; Adrian Kantrowitz, Auburn Hills, both of Mich.

[73] Assignee: L. Vad Technology, Inc., Detroit, Mich.

[21] Appl. No.: 856,904

[22] Filed: May 15, 1997

[51] Int. Cl.$^6$ .................................................. A61B 5/00
[52] U.S. Cl. ............................... 600/485; 600/500; 623/3
[58] Field of Search ..................................... 600/485, 486, 600/488, 490, 493–6, 500–503, 748; 623/3

[56] References Cited

U.S. PATENT DOCUMENTS

| | | | |
|---|---|---|---|
| 4,712,563 | 12/1987 | Link ......................................... | 600/494 |
| 4,741,328 | 5/1988 | Gabbay ..................................... | 600/18 |
| 4,781,715 | 11/1988 | Wurzel ..................................... | 623/3 |
| 4,782,817 | 11/1988 | Singh et al. . | |
| 4,785,795 | 11/1988 | Singh . | |
| 4,877,035 | 10/1989 | Bogen et al. ........................... | 600/486 |
| 4,888,011 | 12/1989 | Kung et al. . | |
| 4,902,272 | 2/1990 | Milder et al. . | |
| 5,045,051 | 9/1991 | Milder et al. . | |
| 5,048,532 | 9/1991 | Hickey .................................... | 600/500 |
| 5,089,016 | 2/1992 | Millner et al. . | |
| 5,352,180 | 10/1994 | Candelon et al. ......................... | 623/3 |

Primary Examiner—Robert L. Nasser
Attorney, Agent, or Firm—Young & Basile, P.C.

[57] ABSTRACT

An apparatus and method for measuring the blood pressure of a patient with a permanent or temporary cardiac assist device throughout an entire cardiac cycle by partially filling the inflatable chamber of the cardiac assist device operatively disposed with respect to an aorta with pressurized fluid and using the partially filled chamber as a transducer. An external pressure sensor is located in a drive unit connected to the inflatable chamber. The drive unit controls, monitors and stores the fluid pressure with respect to the inflatable chamber. When isolated from a pressurized fluid reservoir, the pressure within the inflatable chamber corresponds to the current blood pressure of the patient throughout the cardiac cycle. The inflatable chamber preferably is defined at least in part by a flexible membrane. The inflatable chamber is partially inflated with a predetermined volume of pressurized fluid from the reservoir. The partially inflated chamber is then isolated from the reservoir for at least one complete cardiac cycle, and preferably two complete cardiac cycles. The blood pressure wave form of the patient is continuously monitored and stored by measuring the pressure variations in the isolated, partially filled, chamber. A control program evaluates the stored pressure data and updates a patient parameter table with current heart function parameters for subsequent use during the next series of diastolic augmentation, inflation/deflation cycles of the inflatable chamber.

20 Claims, 3 Drawing Sheets

EXTERNAL BLOOD PRESSURE SENSOR APPARATUS AND METHOD

FIELD OF THE INVENTION

The invention is an apparatus and method for monitoring blood pressure in connection with the use of a cardiac assist device.

BACKGROUND OF THE INVENTION

Congestive heart failure remains one of the major causes of mortality and morbidity in the general population and is growing in magnitude. It affects more than 2 million Americans and consumes several billion dollars in hospitalization. Numerous well-controlled randomized trials have shown that, in many cases, vasodilator therapy has not only improved the quality of life in these patients but has prolonged their survival as well. Nevertheless, a sizeable subset of patients in chronic heart failure do not respond to pharmacologic therapy. Furthermore, while cardiac transplantation has developed into an effective treatment modality for end-stage cardiac failure, its wide application has been limited by the inadequate supply of donor hearts. Therefore, effective therapy which improves the quality of life of these patients while simultaneously increasing their longevity remains a major challenge.

One implementation of a cardiac assist device in the form of a blood pump or balloon is a device which is temporarily inserted or permanently surgically implanted in the aorta to augment the pumping action of the heart. The device is a flexible bladder which is inflated and deflated in synchronism with diastole and systole to elevate aortic blood pressure immediately after aortic valve closure. Inflation and deflation of the bladder can be accomplished by a supply tube which leads to an external source of fluid pressure. In the case of the permanent versions the bladder is connected to a percutaneous access device (PAD) which is likewise permanently surgically implanted in a patient's body to provide a device-tissue interface through the skin of the patient for externally connecting the supply tube to a fluid pressure source. Electrical leads from electrodes are projected through the skin via the percutaneous access device (PAD) and the R wave of the electrocardiograph is monitored to control the fluid pressure source during inflating and deflating cycles of the pump in synchronism with the natural heart beat actions.

By inflating the cardiac assist device during diastole and deflating the device during systole, the load on the left ventricle is reduced and the aortic pressure is raised to increase the blood flow to the coronary arteries. It is therefore essential that cardiac motion be sensed accurately to enable the device to be inflated and deflated correctly in accordance with the cardiac cycle.

A way to sense cardiac motion is to measure the aortic pressure wave form and determine the occurrence of the dicrotic notch, which indicates when the aortic valve closes. The direct method to measure aortic pressure requires that a sensor be permanently implanted within the patient. The long term reliability of such sensors is inadequate at this time.

SUMMARY OF THE INVENTION

Accordingly, it is desirable in the present invention to provide an apparatus and method for accurately sensing the blood pressure wave form within the aorta. In addition, it is desirable in the present invention to control the inflation and deflation timing of the blood pump or other cardiac assist device by periodically monitoring the aortic pressure for a selected number of heartbeats, storing the monitored aortic pressures, and adjusting the operational parameters of inflation and deflation of the blood pump for each subsequent heartbeat in accordance with the stored aortic pressure. It is further desirable in the present invention to provide an apparatus suitable for practicing the foregoing method.

The invention is applicable to a permanent blood pump that is sutured into the wall of the aorta, as well as a temporary balloon pump introduced into the aorta in the vicinity of the heart. In the first configuration, a flexible internal fluid conduit is implanted in a patient and extends from an implanted internal permanent blood pump device to a percutaneous access device (PAD) implanted beneath and projecting through the patient's skin. The PAD allows the implanted blood pump to be operatively connected to or disconnected from an external gas handling means and control means. In the second configuration, a temporary balloon pump can be inserted into the aorta through the femoral artery of a patient's leg. The temporary balloon pump has a relatively thin flexible tube extending externally of the patient through the incision in the patient's leg for connection to an external gas handling means and control means. In either case, an elongated fluid conduit is provided and connectible at one end to an inflatable member operably disposed within a patient with respect to the aorta and connectible to drive means for controlling inflation and deflation cycles of the inflatable member at an opposite end.

Control means is provided for measuring arterial pressure of the patient for a specific number of heartbeats during a test procedure, referred to as a scheduled pressure measurement. The control means further provides for adjusting the inflation and deflation rates of the pump for subsequent heartbeats in accordance with a program stored in memory of the control means based on the arterial pressure measured during the scheduled pressure measurement. Gas handling means is provided for inflating and deflating the pumping bladder in accordance with the evaluation of the arterial pressure measured by the control means.

The control means is available in two drive unit configurations. One is a battery powered wearable drive unit and the other is a line powered drive unit capable of continuous operation. The wearable drive unit is designed to be a portable, battery operated drive unit of minimum size and weight. The control means for both configurations includes means to monitor an ECG signal, pressure sensor means for monitoring the arterial pressure for a specified number of heartbeats, means for detecting the occurrence of the dicrotic notch, and means for measuring the time interval between the detected R wave and the dicrotic notch value. The control means further calculates fluid pressure adjustment for the inflation and deflation of the bladder. The gas handling means can include filtering means, means for pressurizing and depressurizing the bladder, and valves for regulating the flow of gas to and from the blood pump.

The inflatable chamber of the cardiac assist device is disposed in a desired location with respect to the aorta of the patient. After connection of the inflatable chamber of the cardiac assist device to the drive means, a scheduled pressure measurement procedure is conducted. During the pressure measurement procedure, the pump is only partially filled with gas. The control means controls the volume of air delivered to partially fill the pump or balloon. The volume of gas delivered to the pump is calculated by monitoring the pressure drop across an inflation valve over an interval of time. Integrating the pressure drop with respect to time provides a value corresponding to the total volume of gas delivered to the pump. The total volume is monitored so that it does not exceed a predetermined value. When the cardiac assist device is partially filled with gas, the inflation valve is closed to isolate the pump or balloon chamber from the drive means while in a partially inflated condition. The pressure of the gas in the chamber reflects the aortic pressure of the patient when partially inflated and isolated from the drive means. This state is preferably maintained for two heartbeats. The pressure of the chamber is monitored continuously by a pressure sensor in the control means for each heartbeat of the desired number of heartbeats to be monitored. A wave form of the aortic pressure of the heartbeat is stored in memory of the control means. At the same time, an ECG signal is also monitored and stored in memory of the control means. During the scheduled pressure measurement period, a control program stored in memory of the control means computes the systolic time interval, which is the elapsed time from the beginning of the QRS wave of the ECG signal to the closing of the aortic valve as indicated by the dicrotic notch of the aortic pressure. The ventricle assist control program uses the information provided during the scheduled pressure measurement procedure to adjust the inflation volume and timing for subsequent heartbeats. The scheduled pressure measurement procedure is repeated at scheduled time intervals and/or with changing heart rate conditions. The time intervals and/or heart rate parameter conditions are fully programmable by the attending physician within preselected ranges and are stored in a patient parameter table located in memory of the control means.

Other objects, advantages and applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DESCRIPTION OF THE PREFERRED EMBODIMENT

The present invention relates to an apparatus and method for measuring blood pressure in a patient who is receiving diastolic augmentation. Various diastolic augmentation systems and devices are currently known. The present invention is particularly adapted for use with an inflatable chamber of the type, permanently or temporarily, disposed in the descending thoracic aorta region of a patient. For example, U.S. Pat. No. 4,630,597 issued Dec. 23, 1986 and U.S. Pat. No. 4,051,840 issued Oct. 4, 1977 disclose details of a permanent implanted pump apparatus which is incorporated herein by reference. In addition, U.S. Pat. No. 3,585,983 issued Jun. 22, 1971, U.S. Pat. No. 4,692,148 issued Sep. 8, 1987, U.S. Pat. No. 4,733,652 issued Mar. 29, 1988, U.S. Pat. No. 4,809,681 issued Mar. 7, 1989 and U.S. Pat. No. 5,169,379 issued Dec. 8, 1992 each disclose details of a temporary intra-aortic balloon pump system which are also incorporated herein by reference.

Figure 1:
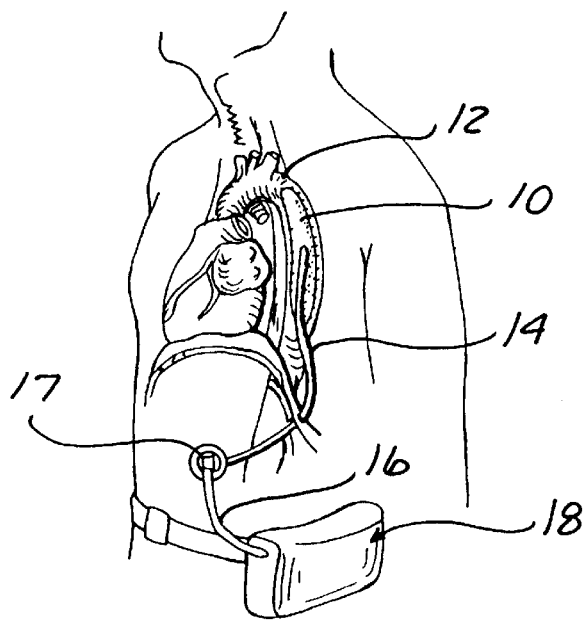
FIG. 1 is a schematic view of major components of a permanent cardiac assist device connected to drive means for controlling the device according to the present invention.
Figure 2:
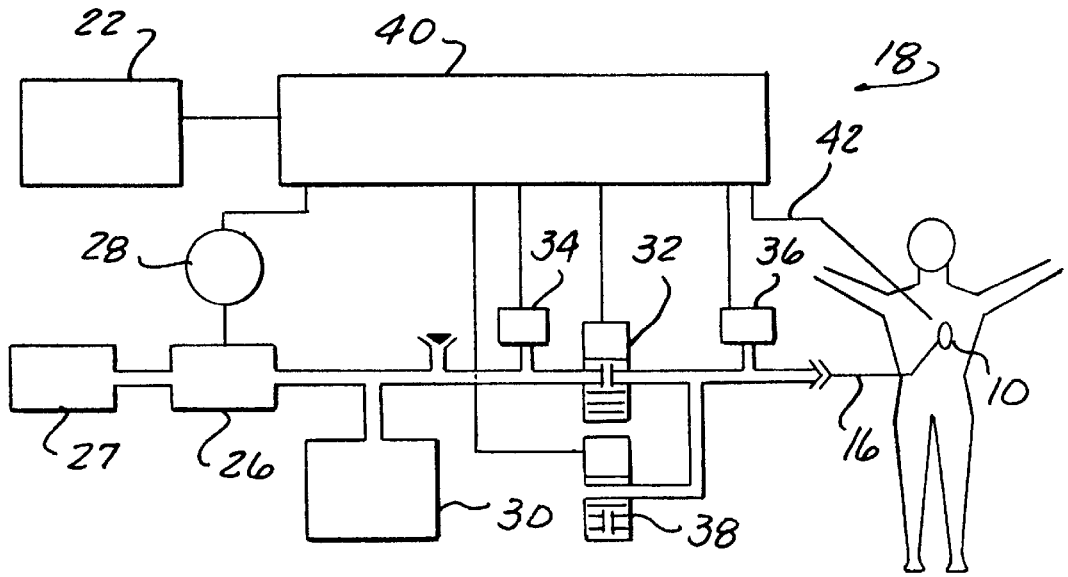
FIG. 2 is a schematic diagram of a wearable drive means for controlling the cardiac assist device.
Figure 3:
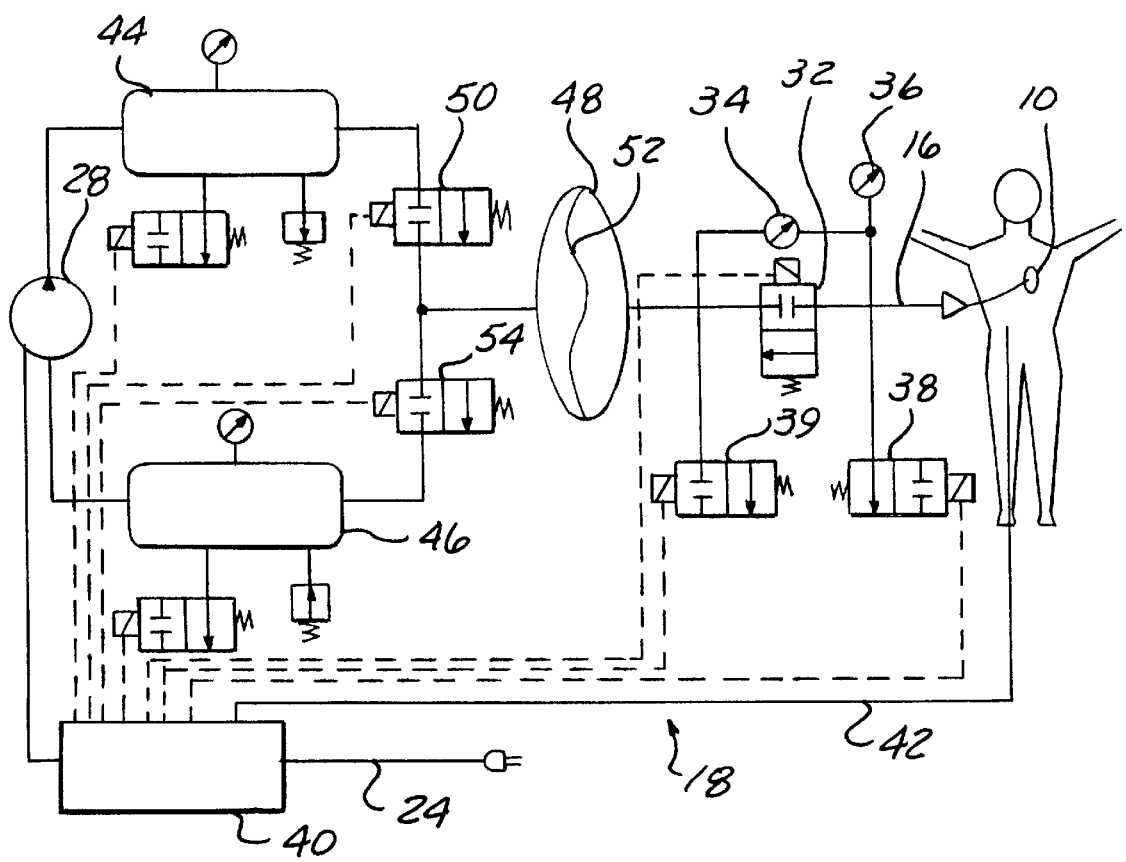
FIG. 3 is a schematic diagram of a line powered drive means for controlling either a permanent or a temporary cardiac assist device.

Major components of a cardiac assist system are shown in FIG. 1. In the preferred embodiment, a permanent blood pump 10 is sutured into the wall 12 of the descending thoracic aorta. An internal drive line or flexible fluid conduit 14 is operably connected between the implanted device 10 and a percutaneous access device (PAD) 17 implanted beneath and projecting through the patient's skin, typically in the abdominal area. An external device line or flexible fluid conduit 16 may be operatively connected to or disconnected from an external drive means 18 for controlling cyclical diastolic augmentation in response to periodic blood pressure measurements obtained automatically from the patient. The drive means 18 generally includes a controller and gas handling means. The drive means 18 conveys pressurized fluid, such as air, to power and to control the timing of inflation and deflation of an inflatable chamber 10, such as the permanently implanted pump. There are two configurations of drive means 18 illustrated with respect to the present invention, a wearable battery-powered unit (FIG. 2), and a line-powered unit (FIG. 3). Each drive means 18 uses an electrocardiogram (ECG) signal 42 for synchronization.

The wearable drive unit (FIG. 2) is designed to be a portable, battery operated drive unit of a minimum size and weight to allow mobility. The battery pack 22 is chosen as a trade-off between weight and operation time. One hour is the nominal operating time on batteries, given charge density limitations of current battery technologies. The wearable drive unit includes a compressor 26 run by motor 28 for drawing air through a filter unit 27. A pressure reservoir 30 communicates with a normally closed control valve 32. Control valve 32 has an upstream pressure sensor 34 and a downstream pressure sensor 36. During inflation, a normally open deflation valve 38 is closed and control valve 32 is opened to allow passage of pressurized fluid. Valve 32 functions as a metering orifice while open. Differential pressure across valve 32 is measured and accumulated in memory. The accumulated differential pressure value correlates to a volume of pressurized fluid entering the inflatable chamber of pump 10. The measured differential pressure is proportional to flow velocity, and if the flow velocity is known over a fixed increment of time, then it is also proportional to volume. A comparison of the accumulated differential pressure to a predetermined value that takes into consideration all of the constant values, conversion factors and the like, provides a determination of whether the desired volume of fluid has passed through the valve orifice. The normally open deflation valve 38 is deenergized to permit expulsion of pressurized fluid from the inflatable chamber to atmosphere in response to the patient's natural blood pressure to deflate the chamber. A controller, essentially indicated at 40, controls the above components, monitors the ECG signal 42, as well as provides storage for a control program and information monitored during the pressure measurement procedure.

Referring now to FIG. 3, standard line voltage 24 provides a continuous source of power for the line powered drive unit (LPDU). The line powered drive unit is capable of continuous operation. The line powered drive unit may also include a battery backup system (not shown) to maintain operation in the event of main power interruptions. The LPDU system can operate on the backup battery for up to 6 hours. The LPDU (FIG. 3) has essentially the same components as the wearable drive unit of FIG. 2, but is in a closed loop drive configuration. The closed loop drive is driven by the pressure differential between a pressure reservoir 44 and a vacuum reservoir 46. An isolation chamber 48 is fluidly connected to the two reservoirs and functions to provide increased safety features with respect to the fluid medium for driving the cardiac assist device 10. Alternatively, the closed shuttle gas loop drive illustrated in FIG. 3 can be used with an intra-aortic balloon pump for temporary left ventricular assistance, where the inflatable balloon or chamber is mounted on a catheter and inserted percutaneously usually via the femoral artery into the descending aorta. The balloon catheter is connected to a closed loop drive, such as that illustrated in FIG. 3, which provides fluid power. The fluid power medium in the temporary intra-aorta balloon pump is usually a helium based closed shuttle gas loop line-powered drive system rather than an air based line-powered drive unit due to the small diameter of the catheter connecting to the intra-aortic balloon. A source of helium (not shown) can be connected through valve 39 to fill the closed shuttle gas loop of the temporary intra-aorta balloon pump. In any case, whether using helium, air or other suitable fluid or combination of fluids, by opening and closing valves 50 and 54, a movable member 52 in the isolation chamber 48 will move to inflate or deflate the cardiac assist device 10. When the normally closed control valve 32 is opened, fluid in the cardiac assist device side of isolation chamber 48 is permitted to flow back and forth through the open aperture of control valve 32. Valve 32 is operated between an open position and a closed position in response to relative positions of valves 50 and 54. When valve 50 is open and valve 54 is closed, the isolation chamber 48 is preloaded with pressurized fluid from the closed loop drive system. When control valve 32 is actuated, the preloaded, pressurized isolation chamber drives the moveable member in one direction to force fluid through the open aperture of control valve 32 into the inflatable chamber of pump 10. Control valve 32 can then be de-energized to isolate the inflatable chamber from the drive means 18. Valve 50 is then closed and valve 54 is opened to draw fluid out of the isolation chamber 48 to preload the isolation chamber with vacuum. When the control valve 32 is opened, the vacuum-preload isolation chamber 48 draws fluid out of the inflatable chamber of the pump 10. The preloading of the isolation chamber 48 cyclically with pressure and vacuum assists in decreasing the response time of the inflatable chamber allowing for faster inflation and deflation. Valves 38 are provided as safety features to permit expulsion of fluid from the inflatable chamber in the case of drive unit failure and includes a second valve between the isolation chamber 48 and control valve 32 for depressurizing the interconnecting fluid conduit. Pressure sensor 34 (FIG. 3) is positioned across valve 32 to measure differential pressure across valve 32 in either direction of fluid flow. Valve 32 functions as a metering orifice so that pressure sensor 34 indicates differential pressure across valve 32 during inflation and deflation. Pressure sensor 36 operates to indicate pressure within the inflatable chamber when isolated from the drive unit by closure of valve 32, and when partially inflated and isolated from the drive unit during the pressure measurement procedure.

Figure 4:
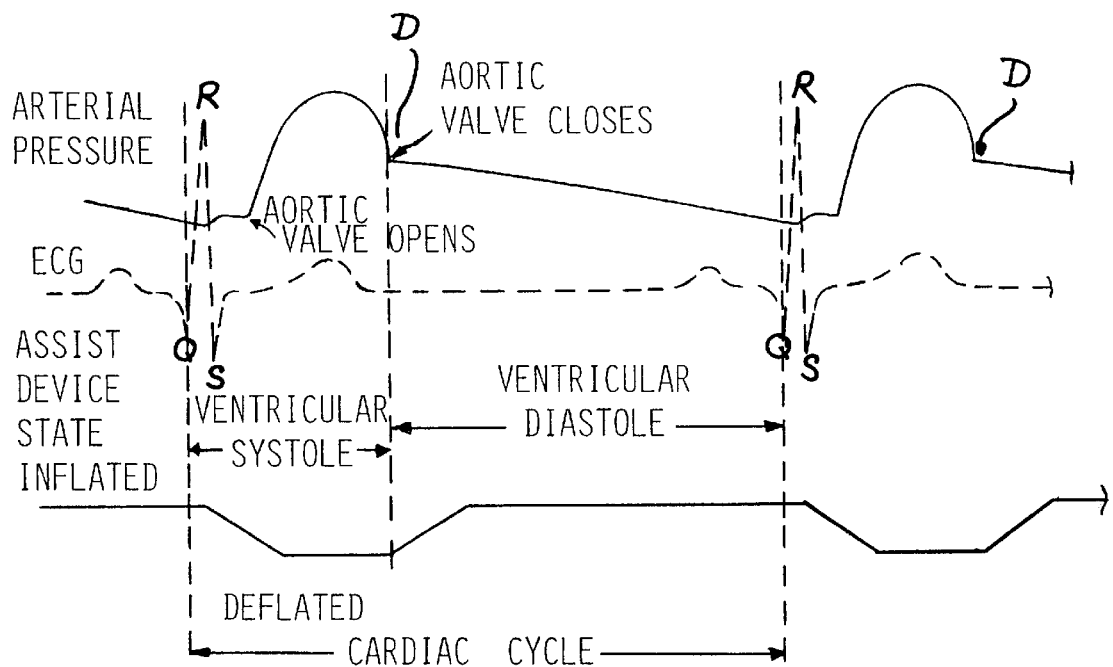
FIG. 4 is a graph showing the relationship of normal aortic blood pressure without assistance, the ECG signal, and assist device inflation state.

The primary function of the drive unit 18 of both the battery operated and line power configurations is to inflate and deflate the cardiac assist device 10 synchronously with the patient's natural heart rhythm or ECG, thereby providing diastolic augmentation to the left ventricle of the heart. The drive unit 18 uses an R wave from the ECG signal 42 and data from an aortic pressure measurement to adjust inflation volume and timing. The invention provides an external means to measure aortic pressure for calculating the systolic time intervals, that is the time from the detection of the QRS complex to the detection of the aortic valve closure, as shown in FIG. 4.

Aortic pressure is measured by measuring the fluid pressure with the pressure sensor 36 when the inflatable chamber 10 is isolated from the drive unit 18 by closure of valve 32 during a periodic pressure measurement procedure. During this procedure, the inflatable chamber is partially inflated and then is temporarily isolated from the drive unit by closing valve 32 for two heart cycles. The pump 10 is partially inflated by closing valve 54 and opening valve 50 which preloads moveable member 52 of isolation chamber 48 to force fluid through control valve 32 when opened. Once the cardiac assist device 10 is inflated to a predetermined volume, valve 50 and control valve 32 close. In this stable isolated condition, the pressure measured by sensor 36 of inflatable chamber 10 corresponds to the blood pressure of the patient. The inflatable chamber is defined at least in part by a flexible membrane. The flexible membrane is held in a flaccid state when the inflatable chamber is partially inflated with a predetermined volume of pressurized fluid allowing the inflatable chamber to act as a transducer. The pump 10 remains partially inflated through at least one normal heartbeat and preferably two complete cardiac cycles. Measured pressure values corresponding to the blood pressure of the patient are stored in memory at predetermined time intervals, for example every 4 milliseconds (msec). During this time interval, an ECG signal is also stored in the controller 40. The time interval starting from when the R wave is detected in the ECG signal to the dicrotic notch (D), as measured by the blood pressure, is recorded as the systolic time interval. When the cyclical inflation/ deflation pumping resumes after the pressure measurement procedure, the blood pump 10 remains evacuated during the systolic interval and then inflates immediately after the closing of the aortic valve (D), based on revised patient parameters stored in memory. The revised patient parameters are generated by the control program stored in memory of the controller based on an evaluation of the previously measured patient parameters and physician definable parameters.

The control program for the systolic time interval measures the time elapsed, in units of 4 milliseconds, from the QRS trigger, as detected from continuously monitoring the digitized ECG signal to the dicrotic notch (D), as detected by measuring blood pressure. The relationship of the blood pressure, ECG signal, and inflation/deflation of the pump 10 is illustrated in FIG. 4. The desired criteria for dicrotic notch (D) detection is a reversal of slope (from negative to positive) occurring within a physician adjusted time window. If not found, detection of negative to zero slope is checked or if that is not found, detection of largest negative slope of a minimum duration is checked. If no notch (D) is detected within the time window, the "Dicrotic notch, default" specified in a patient parameter table stored in the controller 40 is used.

Although the inflation capacity of the pump 10 during the pressure measurement procedure is not critical, it is critical that pump 10 remains flaccid and is not taut. Since cardiac assist devices may vary in volume capacity and in order not to overly inflate the pump 10, a known volume of pressurized fluid is delivered to the pump 10. For a temporary cardiac assist device 10 having a volumetric capacity of 35–40 cubic centimeters (cc) inclusive, a preferred partially inflated volume would be approximately 20 cc. For a permanent cardiac assist device having a volumetric capacity of 55–60 cc, a preferred partially inflated volume would be approximately 30 cc. In general, inflating device 10 to half of its volumetric capacity would be a preferred volume for partial inflation during the pressure measurement procedure. The pressure measurement procedure can be scheduled to occur on a regular periodic basis preferably between every 3–20 minutes during operation of the drive unit, and more preferably approximately every 10 minutes during operation. In addition, or in the alternative, the pressure measurement procedure can take place immediately whenever a predetermined change in patient parameter occurs. For example, a change in heart rate exceeding a physician adjusted value, such as 20%, of the average of the previously measured values. The physician adjusted value is a value between 10% and 80% inclusive. Both the scheduled time interval and the percentage change in patient parameters for triggering the pressure measurement procedure can be physician adjusted and stored in memory, within acceptable windows of values. If the physician attempts to enter a value outside the window, i.e. above the maximum value allowed, or below the minimum value allowed, it is ignored and the default value is used instead. Preferably the pressure measurement procedure is run as a first initial start up procedure, when the drive unit is first connected and turned on, to test the patient's current status and to modify the operating characteristics accordingly. During the time period when the inflation valve 50 and control valve 32 are open, the controller 40 measures the differential pressure across control valve 32 and accumulates the differential pressure measurements over time which corresponds to the volume of pressurized fluid delivered to the inflatable chamber 10. When the accumulated sum of the differential pressure measurements reaches or exceeds a predefined value, the control valve 32 is closed.

Figure 5:
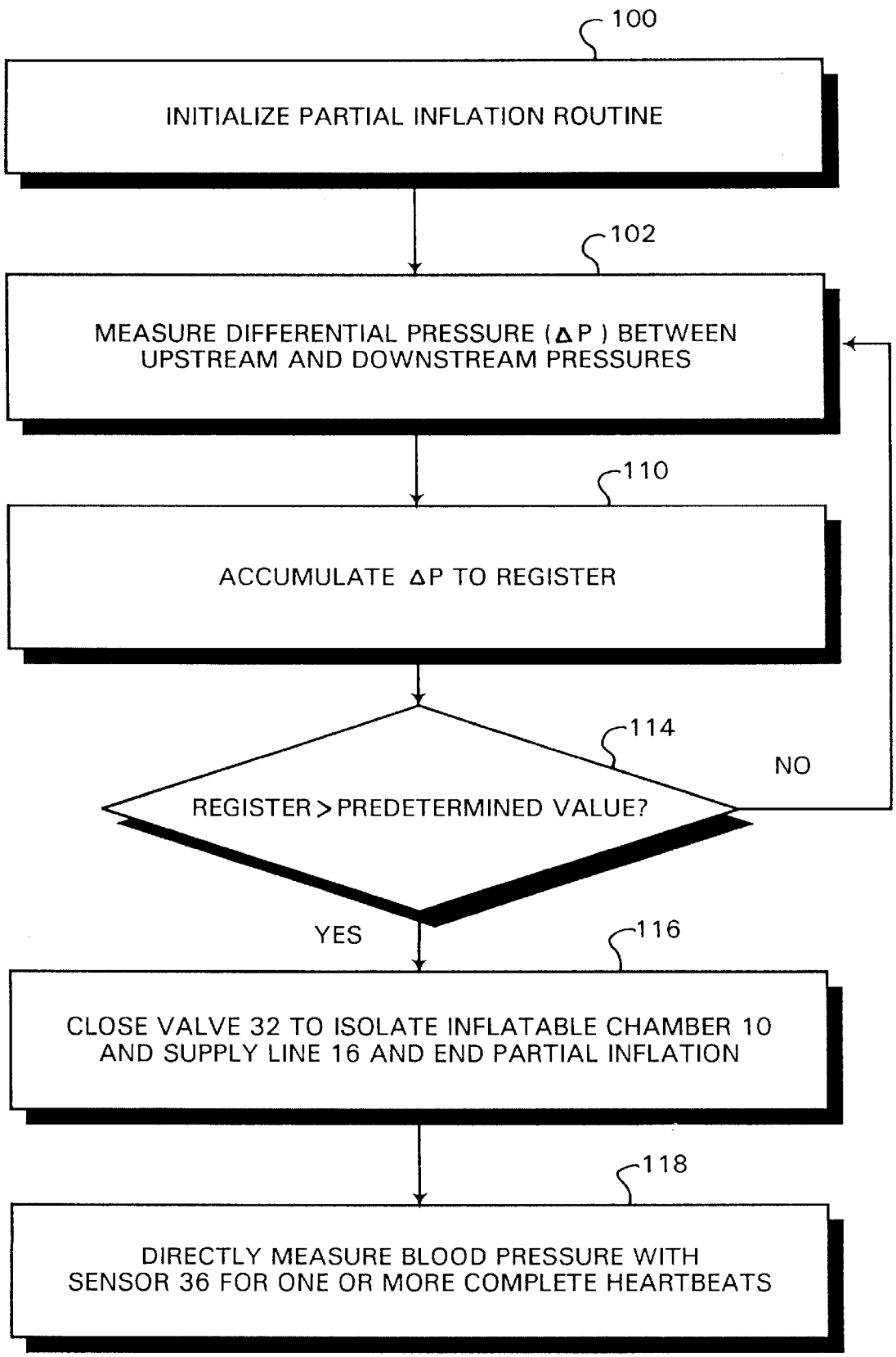
FIG. 5 is a flow chart illustrating control program steps to partially inflate the cardiac assist device during a pressure measurement procedure.

FIG. 5 shows a simplified flow chart for the control program of controller 40 when inflating pump 10 to a predetermined volume. Step 100 initializes the partial inflation routine of the program to partially inflate cardiac assist device 10 to a predetermined volume, typically including setting storage registers to zero and other values to their respective defaults. Deflation valve 54 has been closed previously. Inflation valve 50 has been open previously and then control valve 32 is opened to begin inflating the inflatable chamber. During inflation, when control valve 32 is open, the control valve 32 functions as a metering orifice. Step 102 measures a differential pressure between upstream pressure sensor 34 and downstream pressure sensor 36. The differential pressure (ΔP) is accumulated over time in a memory register at step 110. For the line power drive unit of FIG. 3 the differential pressure is measured directly by sensor 34. Step 110 accumulates the differential pressure measurement corresponding to the accumulated incremental volume to contents of the memory register. The memory register is then evaluated to determine whether the accumulated differential pressure measurements are greater than a predetermined value in step 114. If the memory register is not greater than the predetermined value, the routine returns to step 102. If the memory register is greater than the predetermined value, then the inflatable chamber is sufficiently, partially inflated in order to continue the scheduled pressure measurement procedure.

Within the environment of the patient, the fluid pressure in the partially inflated flaccid pump 10 correspondingly mirrors the arterial pressure. The pressure sensor 36 measures pressure within the partially inflated, inflatable chamber of pump 10 corresponding to the arterial pressure of the patient. Once the pump 10 is partially filled with the predetermined volume of pressurized fluid, the pump 10 is allowed to settle and inflation valve 50, deflation valve 38 and control valve 32 are closed, corresponding to step 116. Settling equalizes pressures throughout the isolated inflatable chamber 10 and on either side of the membrane of pump 10, allowing the isolated inflation chamber 10 to act as a pressure transducer. The controller 40 measures the aortic pressure wave form based on pressure measurements of sensor 36 and takes sample pressure readings approximately every four milliseconds, for at least one cardiac cycle during the scheduled pressure measurement procedure and preferably during two complete cardiac cycles, corresponding to step 118. Preferably, measurements are taken over two heartbeats to allow verified wave form measurement and analysis.

Based on the stored information of the cardiac cycle, taken during the scheduled pressure measurement procedure, the dicrotic notch (D) can be detected from a reversal of slope occurring within a physician adjusted time window. If not found, detection of negative to zero slope is checked or if that is not found, detection of largest negative slope of a minimum duration is checked. If no notch (D) is detected within the time window, the "Dicrotic notch, default" specified in a patient parameter table stored in the controller 40 is used. The controller 40 also monitors the QRS complex from the ECG signal taken during the scheduled pressure measurement procedure. From this stored information, controller 40 computes the time from the QRS complex or R-wave to the dicrotic notch (D) as the systolic time interval. As a result, pumping begins with up-to-date patient information. The detection of the aforementioned events can be adjusted or overridden by a physician within safety parameter windows, if the patient has special needs. These parameters are stored in the non-volatile memory of the controller 40. Pumping continues with the defined parameters until another timing update is mandated. The scheduled pressure measurement is executed at a time interval of ten minutes as a default, or other programmable time interval ranging from three to twenty minutes. The schedule pressure measurement procedure can be requested ahead of schedule, if the heart rate changes by more than 20% or other physician programmable change of 10%–80%.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A method for sensing blood pressure during a cardiac cycle of a patient having a cardiac assist device with an inflatable chamber operably disposed with respect to an aorta of the patient comprising the steps of:

partially inflating the inflatable chamber with a predetermined volume of fluid delivered from a source of pressurized fluid, wherein the inflatable chamber is defined at least in part by a flexible membrane and the flexible membrane is flaccid when partially inflated with said predetermined volume of fluid;

isolating the inflatable chamber from the source of pressurized fluid; and measuring pressure in the inflatable chamber with a pressure sensor located external with respect to the chamber, wherein pressure in the inflatable chamber corresponds to blood pressure of the patient.

2. The method of claim 1 further comprising the step of:

storing the measured pressure wave form over time of the inflatable chamber for at least one cardiac cycle.

3. The method of claim 1 wherein the step of partially inflating the inflatable chamber further includes the step of:

measuring a differential pressure across an inflation valve disposed between the inflatable chamber and said source of said pressurized fluid.

4. The method of claim 3 wherein partially inflating the inflatable chamber further includes the steps of:

accumulating the volume delivered during each sampling time interval; and comparing accumulated volume to a predetermined volume value.

5. The method of claim 4 wherein partially inflating the inflatable chamber further includes the step of:

closing an inflation valve when the accumulated volume delivered to the inflatable chamber is at least equal to said predetermined volume value.

6. An apparatus for sensing blood pressure during a cardiac cycle of a patient having a cardiac assist device with an inflatable chamber adapted to be operatively disposed with respect to an aorta of the patient comprising:

means for partially inflating the inflatable chamber with a predetermined volume of fluid delivered from a source of pressurized fluid, wherein the inflatable chamber is defined at least in part by a flexible membrane and the flexible membrane is flaccid when partially inflated with said predetermined volume of fluid;

means for isolating the inflatable chamber from the source of pressurized fluid; and means for measuring pressure in the inflatable chamber with a pressure sensor located external with respect to the chamber, wherein pressure in the inflatable chamber corresponds to blood pressure of the patient.

7. The apparatus of claim 6 further comprising:

means for storing the measured pressure wave form over time of the inflatable chamber for at least one cardiac cycle.

8. The apparatus of claim 6 further comprising:

means for measuring a differential pressure across an inflation valve disposed between the inflatable chamber and said source of said pressurized fluid.

9. The apparatus of claim 8 wherein said means for measuring differential pressure across the inflation valve further comprises:

a first pressure sensor located upstream of the inflation valve; and a second pressure sensor located downstream of the inflation valve.

10. The apparatus of claim 6 wherein the source of pressurized fluid further comprises:

a pressure reservoir for containment of a quantity of gas under pressure.

11. An apparatus for periodically sensing blood pressure during a cardiac cycle of a patient having a cardiac assist device with an inflatable chamber adapted to be operatively disposed with respect to an aorta of the patient and for assisting the cardiac cycle of the patient between periodic blood pressure sensing comprising:

means for partially inflating the inflatable chamber with a predetermined volume of fluid delivered from a source of pressurized fluid, wherein the inflatable chamber is defined at least in part by a flexible membrane and the flexible membrane is flaccid when partially inflated with said predetermined volume of fluid;

means for isolating the inflatable chamber from the source of pressurized fluid;

means for measuring pressure in the inflatable chamber with a pressure sensor located external with respect to the chamber, wherein the pressure in the inflatable chamber corresponds to blood pressure of the patient; and drive means for cyclically controlling an inflation/deflation cycle of the inflatable chamber in response to patient parameters relating to heart function including pressure determined by the pressure measuring means, said drive means having at least one inflation valve, at least one deflation valve, and control means for selectively opening and closing said valve.

12. The apparatus of claim 11 further comprising:

the drive means for cyclically inflating and deflating the inflatable chamber with a pressurized gaseous fluid synchronously with a heart beat of the patient based on a first set of programmable patient parameters relating to heart function;

means for periodically conducting a pressure measurement procedure; and for updating patient parameters to thereafter, cyclically inflate and deflate the inflatable chamber with pressurized gaseous fluid according to the updated patient parameters until modified by another pressure measurement procedure.

13. The apparatus of claim 11 further comprising:

means for selectively scheduling the pressure measurement procedure for execution at a time interval ranging from three minutes to twenty minutes, inclusive.

14. The apparatus of claim 11 further comprising:

means for selectively scheduling a pressure measurement procedure, if a heart rate of the patient changes by more than a preselected percentage value of an average of a predetermined number of previously measured heart rate values, the preselected percentage value selected in a range between 10% to 80%, inclusive.

15. A method for sensing blood pressure during a cardiac cycle of a patient having a cardiac assist device with an inflatable chamber operatively disposed with respect to an aorta of the patient comprising the steps of:

cyclically inflating and deflating the inflatable chamber with a pressurized gaseous fluid synchronously with a heart beat of the patient based on a first set of programmable patient parameters relating to heart function;

periodically conducting a pressure measurement procedure, wherein the procedure includes the steps of:

partially inflating the inflatable chamber with a predetermined volume of pressurized gaseous fluid;

isolating the inflatable chamber from said source of pressurized gaseous fluid and allowing the inflatable chamber to settle so that the inflatable chamber acts as a transducer;

measuring pressure in the inflatable chamber with an external pressure sensor, wherein said pressure in the inflatable chamber corresponds to current blood pressure of said patient;

monitoring pressure in the inflatable chamber for at least one complete cardiac cycle;

storing said monitored pressure values in memory of a controller; and updating patient parameters based on said stored pressure values; and thereafter, cyclically inflating and deflating the inflatable chamber with pressurized gaseous fluid according to the updated patient parameters until modified by another pressure measurement procedure.

16. The method of claim 15 wherein the partial inflating step further comprises the steps of:

delivering pressurized fluid to the inflatable chamber through an inflation valve;

measuring a differential pressure across the inflation valve; and integrating the differential pressure with respect to a time interval corresponding to an amount of time the inflation valve is in an open position to determine a volume of fluid delivered to the inflatable chamber.

17. The method of claim 15 wherein the conducting step is performed at predetermined time intervals.

18. The method of claim 15 further comprising the steps of:

monitoring a heart beat rate of the patient; and performing the conducting step immediately, if a monitored change in heart beat rate of the patient exceeds a predetermined percentage.

19. The method of claim 15 further comprising the step of:

selectively scheduling the pressure measurement procedure for execution at a time interval ranging from three minutes to twenty minutes, inclusive.

20. The method of claim 18 further comprising the step of:

selectively scheduling a pressure measurement procedure, if a heart rate of the patient changes by more than a preselected percentage value of an average of a predetermined number of previously measured heart rate values, the preselected percentage value selected in a range between 10% to 80%, inclusive.

* * * * *